United States Patent [19]

Connor et al.

[11] 3,932,620

[45] Jan. 13, 1976

[54] **KETONES AND KETOXIMES DERIVED FROM ACID S, AN ANTIBIOTIC PRODUCED BY *POLYANGIUM CELLULOSUM* VAR. *FULVUM***

[75] Inventors: David T. Connor, Parsippany; Samuel M. Ringel, Rockaway; Maximilian von Strandtmann, Rockaway Township, all of N.J.

[73] Assignee: Warner-Lambert Company, Morris Plains, N.J.

[22] Filed: June 24, 1974

[21] Appl. No.: 482,052

[52] U.S. Cl. .............................................. 424/122
[51] Int. Cl.$^2$ ......................................... A61K 35/00
[58] Field of Search .................................... 424/122

[56] References Cited

UNITED STATES PATENTS

| | | | |
|---|---|---|---|
| 3,651,216 | 3/1972 | Ringel et al. | 424/115 |
| 3,804,948 | 4/1974 | Strandtmann et al. | 424/122 |

*Primary Examiner*—Jerome D. Goldberg
*Attorney, Agent, or Firm*—Albert H. Graddis; Frank S. Chow

[57] ABSTRACT

The present invention relates to keto and ketoxime derivatives of the novel antibiotic substance, acid S, produced by the microorganism *Polyangium cellulosum* var. *fulvum* (ATCC N0. 25532) and to processes for their preparation. The novel keto and ketoxime derivatives of acid S of this invention are useful antifungal agents.

6 Claims, No Drawings

KETONES AND KETOXIMES DERIVED FROM ACID S, AN ANTIBIOTIC PRODUCED BY *POLYANGIUM CELLULOSUM* VAR. *FULVUM*

The present invention relates to novel ketones and ketoximes derived from acid S, a potent antibiotic produced by fermentation of the microorganism *Polyangium cellulosum* var. *fulvum* (ATCC No. 25532) in a suitable culture medium. Specifically, the present invention relates to ketoacid S methyl ester, ketoacid S methyl ester oxime and ketoacid S oxime having molecular formulas $C_{26}H_{38}O_2(OH)(CO)CO_2CH_3$, $C_{26}H_{38}O_2(OH)(CNOH)CO_2CH_3$ and $C_{26}H_{38}O_2(OH)(CNOH)CO_2H$, respectively. The present invention also specifically relates to ketodiol S and ketodiol S oxime having molecular formulas $C_{26}H_{38}O_2(OH)(CO)CH_2OH$ and $C_{26}H_{38}O_2(OH)(CNOH)CH_2OH$, respectively. The monoacetate of ketoacid S methyl ester having molecular formula $C_{26}H_{38}O_2(OCOCH_3)(CO)CO_2CH_3$ is also included within the scope of this invention.

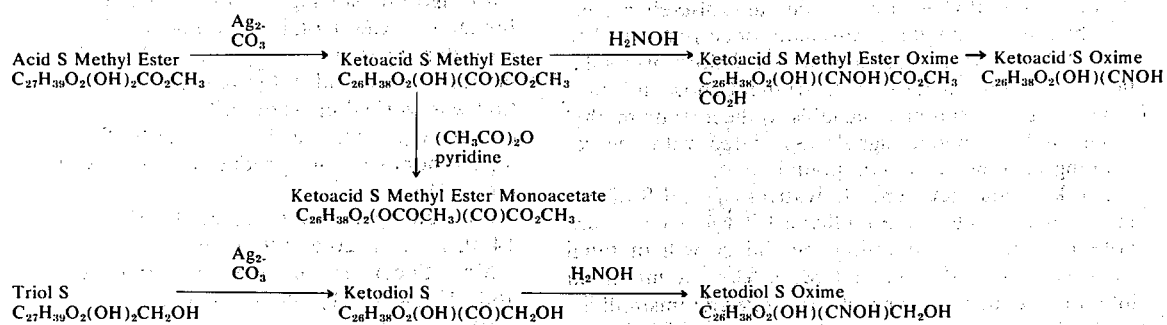

The present invention also relates to processes for the production of the aforementioned keto and ketoxime derivatives of acid S and to therapeutic compositions containing the compounds of this invention. These compositions are particularly useful for the dermatophytic and systemic treatment of fungal disease.

U.S. Pat. No. 3,651,216, issued Mar. 21, 1972 and U.S. Pat. No. 3,804,948, issued Apr. 16, 1974, describes the microbiological production of antibiotics designated A, B and C and acids S and F. These potent antifungals are elaborated when the microorganism *Polyangium cellulosum* var. *fulvum* (ATCC No. 25532) is fermented in a suitable culture medium. The aforementioned patent application also describes the chemical preparation of the methyl esters of acids S and F. Like the corresponding acids, the methyl esters of acids S and F exhibit antifungal activity.

The synthesis of a series of triols, including triol S, from acid S and the corresponding methyl ester by reductive modification of the acid or ester groups of acid S and acid S methyl ester is disclosed in copending U.S. Pat. application No. (our 2100.1035), filed concurrently herewith. These triols are extremely potent antifungals, inhibiting the growth of fungi such as *H. capsulatum*, *I. mentagrophytes* and *M. fulvum* at minimal inhibitory concentrations of the order of 0.78 micrograms/milliliter in the serial 2-fold tube dilution evaluation procedures outlined in U.S. Pat. No. 3,651,216.

Acid S, acid S methyl ester and triol S are characterized by the presence of two secondary hydroxyl groups. It has now been found that selective oxidation of one of the secondary hydroxyl groups to a keto function gives rise to a series of keto derivatives of acid S which are also extremely potent antifungal agents. These compounds and the corresponding ketoximes inhibit the growth of various fungi at very low minimal inhibitory concentrations, and like the triols of acid S of copending Patent Application No. (our 2100.1035), filed concurrently herewith, are more effective against a variety of fungi than existing antifungal compounds.

The novel keto and ketoxime derivatives of acid S of this invention are prepared according to the processes shown schematically below:

The preparation of acid S methyl ester by esterification of acid S, produced when *Polyanguim cellulosum* var. *fulvum* is fermented in an appropriate culture medium, is described in U.S. Pat. No. 3,804,948.

According to the present invention, ketoacid S methyl ester is prepared by selective oxidation of one of the two secondary hydroxyl groups of acid S methyl ester. For example, the above selective oxidation is effected when acid S methyl ester is treated with silver carbonate-on-celite in a suitable solvent, such as toluene.

To obtain ketoacid S methyl ester oxime, ketoacid S methyl ester is treated with hydroxylamine hydrochloride in the presence of an acid-acceptor, such as sodium acetate. Ketoacid S methyl ester oxime is hydrolized under basic conditions, preferably 5% aqueous sodium hydroxide, to afford the corresponding acid, ketoacid S oxime.

To secure ketodiol S, triol S is oxidized with silver carbonate-on-celite in a suitable solvent, such as toluene. The corresponding oxime, ketodiol S oxime, is prepared by treatment of ketodiol S with hydroxylamine and sodium acetate as the preferred acid-acceptor.

Ketoacid S methyl ester is characterized by conversion to ketoacid S methyl ester monoacetate. Typically, ketoacid S methyl ester is acetylated by treatment with acetic anhydride in the presence of a tertiary amine, preferably pyridine, as the acid-acceptor.

The compounds of the present invention are characterized by infrared spectroscopy, mass spectrometry and diagnostic thin-layer chromatography.

The infrared spectra of the keto and ketoxime derivatives of acid S of this invention are determined as thin films with an infrared absorption spectrometer equipped with a diffraction grating. In addition to providing spectral evidence confirming the transformations outlined above, the infrared spectra of the compounds of this invention represent a definitive physical characteristic useful for the identification of said compounds.

The mass spectra of the ketones and ketoximes of this invention are measured on a double-focusing high resolution mass spectrometer employing a heated direct insertion probe. Like the aforementioned infrared spectra, the mass spectra of the above ketones and ketoximes provide a definitive physical property useful for identification of these compounds.

The compounds of this invention are examined on thin-layers of silica gel, 85:10:5 ethyl acetate:2-propanol:water being used as the solvent system and iodine as the visualization agent. The aforementioned derivatives of acid S appear as one well-defined spot.

The monoacetate of ketoacid S methyl ester is characterized by infrared spectroscopy and thin-layer chromatography utilizing the aforementioned techniques. Ketoacid S methyl ester monoacetate is also characterized by nuclear magnetic resonance spectroscopy. The 220 MHz spectrum determined as a chloroform solution with a Varion HA-220 instrument shows a 3-proton singlet at 2.15 ppm assignable to the acetate methyl group and resonance signals associated with the remaining protons of the compound.

The keto and ketoxime derivatives of acid S of this invention and ketoacid S methyl ester monoacetate are potent antifungals inhibiting the the growth of fungi such as *H. capsulatum*, and *M. fulvum* at minimum inhibitory concentrations of $10^{-1}$ micrograms/milliliters in the serial 2-fold tube dilution assay described in U.S. Pat. No. 3,651,216.

The compounds of this invention can be formulated with inert excipients into various dosage forms for oral, parenteral and topical administration by methods well-known to those skilled in the pharmacist's art. Tablets, capsules, powders, solutions, suspensions, ointments, gels and creams are included among these dosage forms. For topical administration, the compounds of this invention may be blended with a vehicle such as white petroleum, the weight of the active ingredients being from about 0.1 to 50% of the total weight.

The antifungal ketones, ketoximes and ketoester monoacetates of this invention can be administered orally, parenterally or topically to various mammals, such as dogs, cats and guinea pigs, afflicted with fungal disease. The typical dose is about 0.01 to 100 mg/kg of body weight of the animal.

EXAMPLE 1

Ketodiol S

Silver carbonate on celite (2 g) was added to a solution of triol S (144 mg) in toluene (50 ml). The reaction mixture was refluxed under nitrogen with vigorous stirring for 1 hour. During this time a further 2 g of silver carbonate on celite was added in 1 g portions. The inorganic solids were filtered off and washed with ethyl acetate. The filtrate and washings were evaporated under reduced pressure to give a brown oil. Purification by preparative thin-layer chromatography gave a yellow oil (80 mg, 55%). Diagnostic thin-layer chromatography indicated a pure homogeneous product.

Infrared Spectrum $\nu_{max}$ 3450, 1720, 1670, 1450, 1380, 1270, 1120, 1070 and 980 $cm^{-1}$.

EXAMPLE 2

Ketodiol S Oxime

A solution of ketodiol S (5 mg), hydroxylamine hydrochloride (1 mg) and sodium acetate (1 mg) in absolute ethanol (7 ml) and water (1 ml) was refluxed for 2 hours under nitrogen. The solvents were removed under reduced pressure and the product isolated by preparative thin-layer chromatography to give a white amorphous solid (3 mg).

Infrared Spectrum $\nu_{max}$ 3300, 1460, 1120, 1040 and 980 $cm^{-1}$.

Mass Spectrum m/e (relative intensity) 473 (17), 456 (70), 193 (80) and 165 (100).

EXAMPLE 3

Ketoacid S Methyl Ester

Silver carbonate on celite (2 g) was added to a solution of acid S methyl ester (200 mg) in toluene (100 ml). The reaction mixture was refluxed under nitrogen with vigorous stirring. Further portions of silver carbonate on celite (total amount added 5 g) were added until thin-layer chromatography indicated the absence of starting material in the reaction mixture. The reaction was worked up as described for ketodiol S. Purification by preparative thin-layer chromatography gave a pure homogeneous product as a pale yellow oil (95 mg, 48%).

Infrared Spectrum $\nu_{max}$ 3350, 1740, 1730, 1670, 1450, 1210, 1120 and 980 $cm^{-1}$.

Mass Spectrum m/e (relative intensity) 486 (20), 468 (22), 457 (21), 391 (42), 373 (20), 275 (35), 193 (60) and 165 (100).

EXAMPLE 4

Ketoacid S Methyl Ester Oxime

A solution of ketoacid S methyl ester (40 mg), hydroxylamine hydrochloride (8 mg) and sodium acetate (8 mg) in absolute ethanol (15 ml) and water (4 ml) was refluxed for 30 minutes under nitgrogen. The solvents were removed under reduced pressure to give a brown oil. Purification by preparative thin-layer chromatography gave a pure homogeneous product as a colorless oil (29 mg, 73%).

Infrared Spectrum $\nu_{max}$ 3350, 1740, 1670, 1440, 1270, 1210, 1110, 1030 and 980 $cm^{-1}$.

Mass Spectrum m/e (relative intensity) 501 (9), 484 (29), 193 (100) and 165 (71).

EXAMPLE 5

Ketoacid S Oxime

A solution of 5% aqueous sodium hydroxide (6 ml) was added to a solution of ketoacid methyl ester oxime (18 mg) in methanol (2 ml). The solution was stirred and refluxed for 30 minutes under nitrogen. The methanol was removed under reduced pressure. The aqueous residue was acidified and extracted with $CHCl_3$. The extracts were dried over $MgSO_4$ and evaporated to give a white amorphous solid (10 mg, 57%). Thin-layer chromatography indicated a pure homogeneous product.

Infrared Spectrum $\nu_{max}$ 3300, 1720, 1670, 1120, 1070 and 980 $cm^{-1}$.

EXAMPLE 6

Ketoacid S Methyl Ester Monoacetate

Acetic anhydride (1 ml) was added to a solution of ketoacid S methyl ester (40 mg) in pyridine (3 ml). The solution was allowed to stand at room temperature overnight. The reaction mixture was cooled and methanol was added to decompose the excess acetic anhydride. The solvents were removed under reduced pressure to give a yellow oil. Purification by preparative thin-layer chromatography gave a pure homogeneous product as a pale yellow oil (31 mg).

Infrared Spectrum $\nu_{max}$ 1740, 1450, 1380, 1240, 1080 and 980 cm$^{-1}$.

Nuclear Magnetic Resonance Spectrum (CDCl$_3$) δ 0.7 to 2.0 (multiplet, 22 protons), 2.15 (singlet, 3H), 2.54 (doublet, 1H), 2.57 (quartet, 1H), 2.65 (doublet, 1H), 2.77 (quartet, 1H), 3.05 (multiplit, 1H), 3.70 (singlet, 3H), 3.70 to 4.20 (multiplit, 4H), 4.94 (doublet, 1H), 5.07 (quartet, 1H), 5.26 (doublet, 1H), 5.42 (multiplet, 2H), 5.47 (quartet, 1H) and 5.57 (doublet, 1H).

H = proton

We claim:

1. An antifungal substance, ketodiol S, prepared by treating triol S (1 equivalent) with silver carbonate-on-celite (60 equivalents) in refluxing toluene (500 equivalents) for 1 hour and having the following characteristics:
   a. Infrared Spectrum $\nu_{max}$ 3450, 1720, 1670, 1450, 1380, 1270, 1120, 1070 and 980 cm$^{-1}$;
   b. Molecular Formula $C_{28}H_{42}O_5$; molecular weight 458.

2. An antifungal substance, ketodiol S oxime, prepared by treating ketodiol S (1 equivalent) with hydroxylamine hydrochloride (1 equivalent) and sodium acetate (1 equivalent) and water (10 equivalents in ethanol (100 equivalents) refluxing for 2 hours and having the following characteristics:
   a. Infrared Spectrum $\nu_{max}$ 3300, 1460, 1120, 1040 and 980 cm$^{-1}$;
   b. Mass Spectrum m/e (relative intensity) 473 (17), 456 (70) 193 (80) and 165 (100);
   c. Molecular Formula $C_{28}H_{43}NO_5$; molecular weight 473.

3. An antifungal substance, ketoacid S methyl ester, prepared by treating acid S methyl ester (1 equivalent) with silver carbonate-on-celite (60 equivalents) in refluxing toluene (500 equivalents) until thin-layer chromatography indicated all starting material consumed, and having the following characteristics:
   a. Infrared Spectrum $\nu_{max}$ 3350, 1740, 1730, 1670, 1450, 1210, 1120 and 980 cm$^{-1}$;
   b. Mass Spectrum m/e (relative intensity) 486 (20), 486 (22), 457 (21), 391 (42), 373 (20), 275 (35), 193 (60) and 165 (100);
   c. Molecular Formula $C_{29}H_{42}O_6$; molecular weight 480.

4. An antifungal substance, ketoacid S methyl ester oxime, prepared by treating ketoacid S methyl ester (1 equivalent) with hydroxylamine (1 equivalent) and sodium acetate (1 equivalent) in ethanol (100 equivalents) and water (30 equivalents) refluxing for 30 minutes, and having the following characteristics:
   a. Infrared Spectrum $\nu_{max}$ 3350, 1740, 1670, 1440, 1270, 1210, 1110, 1030 and 980 cm$^{-1}$;
   b. Mass Spectrum m/e (relative intensity) 501 (9), 484 (29), 193 (100) and 165 (71);
   c. Molecular Formula $C_{29}H_{43}NO_6$; molecular weight 501.

5. An antifungal substance, ketoacid S oxime, prepared by treating ketoacid S methyl ester oxime (1 equivalent) with 5% aqueous sodium hydroxide solution at 60° for 30 minutes and having the following characteristics:
   a. Infrared Spectrum $\nu_{max}$ 3300, 1720, 1670, 1120, 1070 and 980 cm$^{-1}$;
   b. Molecular Formula $C_{28}H_{41}NO_6$; molecular weight 487.

6. An antifungal substance, ketoacid S methyl ester monoacetate, prepared by treating ketoacid S methyl ester (1 equivalent) with acetic anhydride (100 equivalents) and pyridine (200 equivalents) at room temperature for 16 hours, and having the following characteristics:
   a. Infrared Spectrum $\nu_{max}$ 1740, 1450, 1380, 1240, 1080 and 980 cm$^{-1}$;
   b. Nuclear Magnetic Resonance Spectrum δ 0.7 to 2.0 (multiplet, 22 protons), 2.15 (singlet, 3H), 2.54 (doublet, 1H), 2.57 (quartet, 1H), 2.65 (doublet, 1H), 2.77 (quartet, 1H), 3.05 (multiplit, 1H), 3.70 (singlet, 3H), 3.70 to 4.20 (multiplit, 4H), 4.94 (doublet, 1H), 5.07 (quartet, 1H), 5.26 (doublet, 1H), 5.42 (multiplet, 2H), 5.47 (quartet, 1H) and 5.57 (doublet, 1H).

* * * * *